Figure 1:
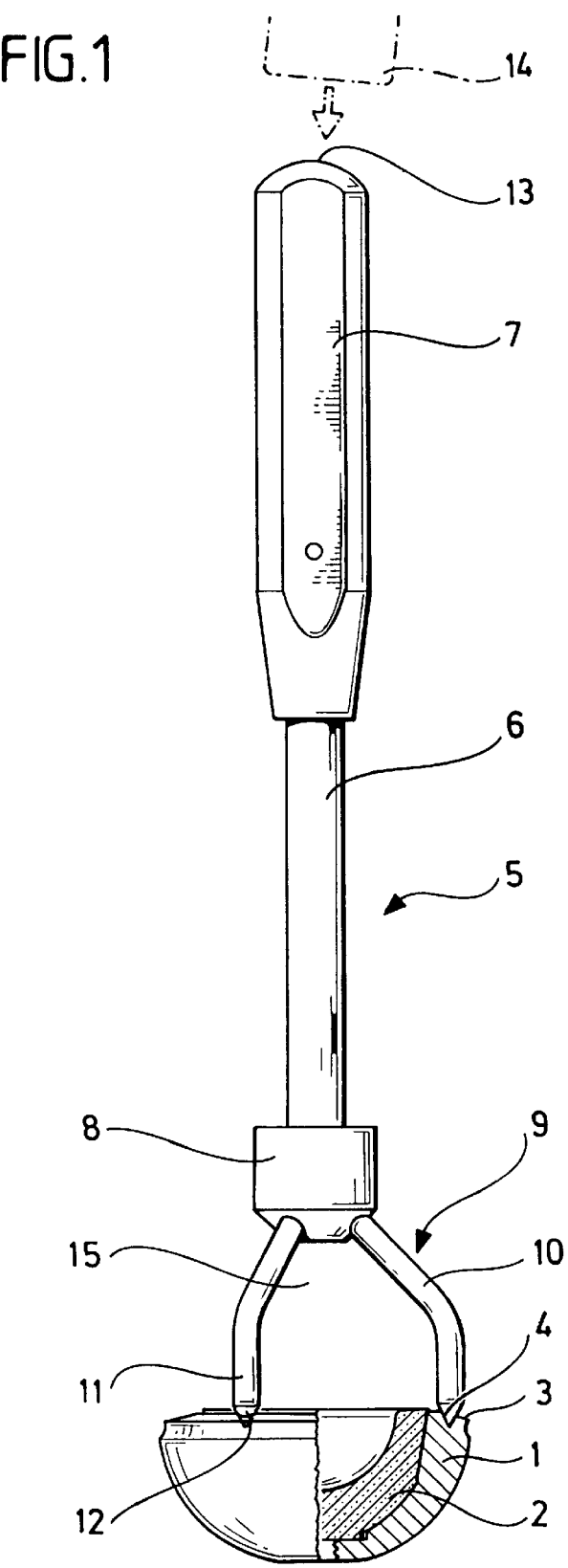

United States Patent
Reu et al.

[11] Patent Number: 6,022,357
[45] Date of Patent: Feb. 8, 2000

[54] SURGICAL INSTRUMENT

[75] Inventors: Gerhard Reu, Tuttlingen; Juergen Strohm, VS-Schwenningen, both of Germany

[73] Assignee: Aesculap AG & Co. KG, Tuttlingen, Germany

[21] Appl. No.: 09/032,233

[22] Filed: Feb. 27, 1998

[30] Foreign Application Priority Data

Mar. 3, 1997 [DE] Germany .................. 197 08 604.7

[51] Int. Cl.[7] .................................................. A61B 17/56
[52] U.S. Cl. ............................... 606/99; 606/86; 606/88; 606/89
[58] Field of Search ................................ 606/86, 88, 89, 606/91, 99

[56] References Cited

U.S. PATENT DOCUMENTS

| | | | |
|---|---|---|---|
| 2,002,021 | 5/1935 | Rouse ........................................ | 606/86 |
| 4,896,663 | 1/1990 | Vandwalls ................................. | 606/79 |
| 5,141,512 | 8/1992 | Farmer et al. ............................. | 606/87 |
| 5,330,481 | 7/1994 | Hood et al. ................................ | 606/86 |
| 5,417,693 | 5/1995 | Sowden ..................................... | 606/99 |
| 5,505,738 | 4/1996 | Hampel et al. ............................ | 606/82 |
| 5,817,098 | 10/1998 | Albrektsson et al. .................... | 606/89 |

FOREIGN PATENT DOCUMENTS 295 16 473  1/1996  Germany .

*Primary Examiner*—Michael Buiz
*Assistant Examiner*—Daphna Shai
*Attorney, Agent, or Firm*—Barry R. Lipsitz

[57] ABSTRACT

A surgical instrument for releasing the press fit of a joint insert in a joint socket is characterized by at least two supports which are positionable on the edge of the joint socket and are connected to a striking surface which is arranged centrally in relation to the joint socket and is oriented away from the open side of the joint socket.

16 Claims, 2 Drawing Sheets

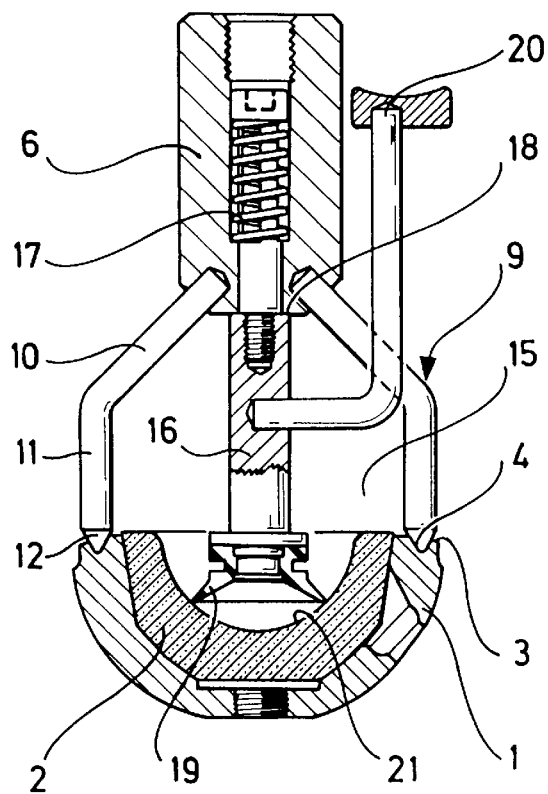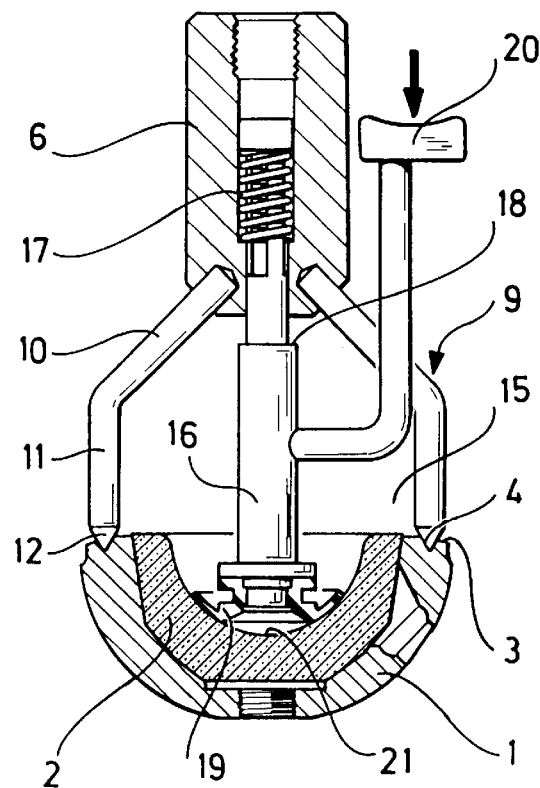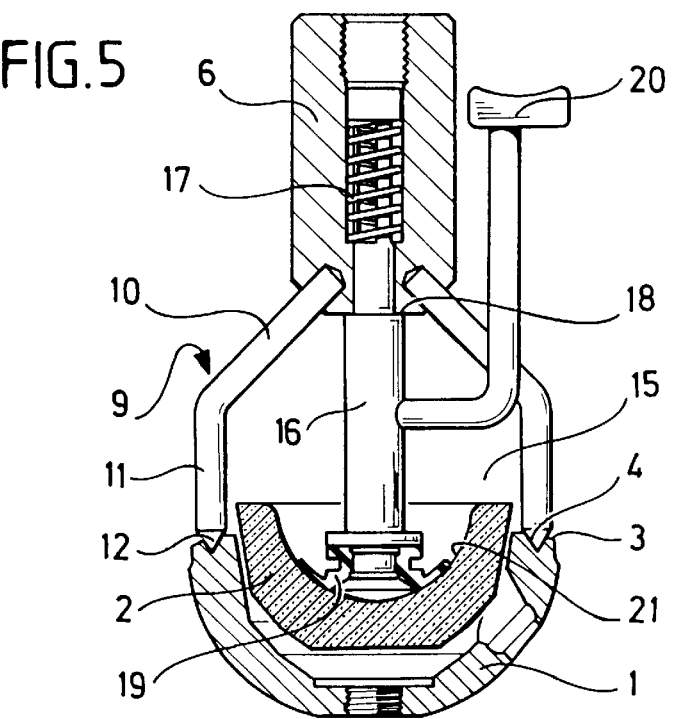

SURGICAL INSTRUMENT

The invention relates to a surgical instrument for releasing the press fit of a joint insert in a joint socket.

Joint inserts are often held by a cone-type press fit in joint sockets, for example, in hip joint sockets. In order to release such joint inserts from the joint socket again, it is either necessary to destroy the joint inserts or to provide special devices on the joint socket which enable ejection of the joint insert from the joint socket. For example, DE 295 16 473 U1 describes a screw arrangement on the joint socket with which the joint insert can be pressed out of the joint socket. However, this makes it necessary for the joint socket to be of appropriate design and for an opening to be left in the joint insert.

The object of the invention is to provide a surgical instrument by means of which the press fit between joint insert and joint socket can be released without any necessity for special structural configurations of the joint insert and the joint socket.

This object is accomplished in accordance with the invention by a surgical instrument of the generic kind which is characterized by at least two supports which are positionable on the edge of the joint socket and are connected to a striking surface which is arranged centrally in relation to the joint socket and is oriented away from the open side of the joint socket.

These supports are placed at the edge of the joint socket and blows are transmitted from the striking surface onto the joint socket via the supports. These blows can be executed by hand with a hammer or with a pneumatically or electrically operated striking tool of a type known per se.

It is known that cone-type press fits can be released under the effect of such blows, and precisely this is to be observed when the described surgical instrument is used. It is of advantage that at least two supports are provided and that the forces are introduced centrally so there is no danger of the joint socket tilting due to it being acted upon on one side or of it deviating under the blows.

In particular, it is expedient for three supports each offset in relation to one another by 120° to be provided, as it is then also ensured that the forces will be introduced precisely in a central direction.

In accordance with a preferred embodiment, provision is made for the supports to form a collecting space for the released insert. At their free end, the supports start at the edge of the joint socket and jointly form a collecting space or cage into which the released joint insert can drop, and so this joint insert is also fixed in its position after release from the instrument and can be removed from this position in a controlled manner by the surgeon.

It is expedient for the supports to have free ends which are insertable into receiving holes at the edge of the joint socket. For example, the supports can be pointed at the free end thereof, and these points can then be inserted into corresponding recesses at the edge of the joint socket so as to ensure a defined positioning of the surgical instrument relative to the joint socket.

In accordance with a preferred embodiment, provision is made for the supports to have sections extending perpendicularly to the plane formed by the edge of the joint socket and adjoining sections oriented towards the center axis of the joint socket. In this way, the supports form the described collecting space for the joint insert and also provide the surgeon with an unimpeded view of the joint socket.

It is advantageous for the supports to be connected to a central shaft which carries the striking surface at its end facing away from the supports. The shaft is preferably surrounded by a handle surface.

In accordance with a preferred embodiment, provision is made for the instrument to comprise a suction holder for the joint insert and for the suction holder to be displaceable in the direction towards the joint socket. This suction holder is fixed by suction on the joint surface of the joint insert and makes it possible for the joint insert which has been released by blows to be subsequently removed from the joint socket. It is expedient for the suction holder to be displaceable in the direction towards the joint socket against the action of a spring. For, once the joint insert is released from the joint socket such a suction holder can lift the joint insert out of the joint socket under the action of the spring.

The suction holder can, for example, carry a sucker.

It is also possible for a device for generating a vacuum, for example, a pump, to be associated with the suction holder, and for the suction holder to thereby adhere by suction to the joint surface of the joint insert.

It is advantageous for the suction holder to have a handle for displacement thereof. With this handle, the surgeon can move the suction holder into an engagement position on the joint insert. Once the joint insert is released, the surgeon recognizes by the movement of this handle, which the suction holder executes under the influence of the action of the spring, that the joint insert is released from the joint socket.

A particularly expedient arrangement is obtained by the suction holder being arranged in the central shaft of the instrument.

In accordance with a preferred embodiment, provision may be made for the striking surface to be designed as a connection piece for a mechanically operated striking tool. This can be, for example, a pneumatically or electrically operated striking tool which is connected at the striking surface to the instrument such that blows generated by the striking tool are transmitted to the instrument. In this context, the term "striking surface" is, therefore, to be understood as including, on the one hand, a surface which a hammer or a similar tool strikes, and, on the other hand, also a part of the instrument which receives and transmits blows generated by a striking tool into the instrument.

Figure 2:
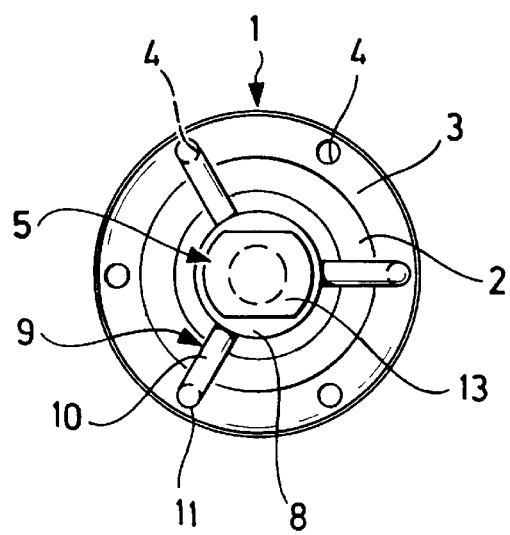

The following description of preferred embodiments of the invention taken in conjunction with the drawings serves for further explanation. The drawings show:

FIG. 1 a side view of a surgical instrument after it has been placed on the edge of a joint socket;

FIG. 2 a plan view of the joint socket of FIG. 1 with the surgical instrument placed thereon;

FIG. 3 a longitudinal view in section of a modified instrument for releasing a joint insert with a suction holder for the joint insert before the suction holder is applied to the joint insert;

FIG. 4 a view similar to FIG. 3 with the suction holder fixed on the joint insert; and FIG. 5 a view similar to FIG. 4 after release of the joint insert from the joint socket.

FIG. 1 shows a metallic joint socket 1 in which a ceramic joint insert 2 is inserted. The joint insert 2 is held in the joint socket 1 by a cone-type press fit.

At the open end, the joint socket 1 terminates in an edge 3 surrounding the joint insert 2, and circular recesses 4 arranged in the edge 3 are offset by 60° in relation to one another in the circumferential direction.

A surgical instrument 5 is used for releasing the joint insert 2 from the joint socket 1. The surgical instrument 5 comprises a central shaft 6 with a handle 7 arranged thereon.

At the free end of the instrument, three supports 9 are held at an enlargement 8 of the shaft 6. The supports 9 first have sections 10 extending outwardly at an incline from the axis of the shaft 6 and adjoining sections 11 extending parallel to the shaft 6. At the free end 12, the supports 9 taper to a point. The three supports 9 are offset by 120° in the circumferential direction and are of such dimensions that the pointed free ends 12 can be inserted into three of the six recesses 4 in the edge 3 of the joint socket 1.

In this position, which is shown in FIG. 1, the shaft 6 is in alignment with the center axis of the joint socket 1.

In this position, the rear end of the handle 7, which is designed as a striking surface 13, can be struck with a suitable tool 14, for example, a hammer, so these blows are transmitted via the instrument 5 onto the joint socket 1. These blows bring about a loosening of the joint insert 2 from the joint socket 1, i.e., the press fit between these two parts is released.

The supports 9 form above the inside space of the joint socket 1 a collecting space 15 in which the released joint insert 2 is captured in such a way that it cannot get lost, and the surgeon can then remove this joint insert 2 in a controlled manner by taking the instrument 5 off the joint socket 1.

The instrument shown partially in FIGS. 3 to 5 is of essentially the same design as the instrument of FIGS. 1 and 2, and like parts are, therefore, given like reference numerals.

In addition to the features shown in FIGS. 1 and 2, a piston 16 is mounted for longitudinal displacement in the shaft 6 of this instrument 5. By means of a helical spring 17 surrounding the piston 16, the piston 16 can be pushed into the shaft 6 and pulled out of it against the action of this spring. The depth to which the piston 16 can be pushed in is limited by a step 18 which strikes the underside of the shaft 6.

The piston 16 protrudes into the collecting space 15 formed by the supports 9 and carries at its free end a sucker 19 which projects into the inside space of the joint insert 2.

Protruding from the side of the piston 16 is a handle 20 which is guided through between two adjacent supports 9 so the piston 16 can be pushed in the direction of the arrow in FIG. 4 against the action of the helical spring 17 by pressure on this handle 20. During this movement, the sucker 19 places itself on the joint surface 21 of the joint insert 2 and attaches itself thereto by suction so the piston 16 remains in the pulled out position and is held therein against the action of the helical spring 17 (FIG. 4).

Once the joint insert 2 is released from the joint socket 1 by the blows on the instrument 5 in the described manner, the helical spring 17 can, however, push the piston 16 into the shaft 6 again, and the joint insert 2 held via the sucker 19 is thereby lifted out of the joint socket 1 (FIG. 5). The surgeon recognizes release of the joint insert 2 from the joint socket 1 by movement of the handle 20 and, after this release of the connection, can remove the instrument 5 with the joint insert 2 held on the sucker 19 from the joint socket 1.

What is claimed is:

1. A surgical instrument comprising:
    at least two supports adapted to be positioned on an edge of a joint socket for releasing the press fit of a joint insert in said joint socket;
    said supports being movably connected via a shaft to a striking surface arranged centrally in relation to said joint socket when said supports are positioned on the edge of the joint socket; and
    said striking surface being oriented away from an open side of said joint socket; wherein a force applied to said striking surface is transmitted to said support via said shaft.

2. A surgical instrument as defined in claim 1 comprising three supports offset in relation to one another by 120°.

3. A surgical instrument as defined in claim 2 wherein said supports form a collecting space for said joint insert when released.

4. A surgical instrument as defined in claim 1 wherein said supports have free ends that are adapted to be inserted into corresponding receiving holes at the edge of said joint socket.

5. A surgical instrument as defined in claim 1 wherein said supports have:
    sections extending perpendicularly to a plane formed by the edge of said joint socket, and
    adjoining sections oriented towards a center axis of said joint socket.

6. A surgical instrument as defined in claim 1 wherein said shaft comprises a central shaft carrying said striking surface at an end facing away from said supports.

7. A surgical instrument as defined in claim 6 wherein at least a portion of said central shaft is surrounded by a handle surface.

8. A surgical instrument as defined in claim 6 further comprising a suction holder for said joint insert, said suction holder being displaceable in a direction towards the joint socket.

9. A surgical instrument as defined in claim 1 further comprising a suction holder for said joint insert, said suction holder being displaceable in a direction towards the joint socket.

10. A surgical instrument as defined in claim 9 wherein said suction holder is displaceable in said direction towards said joint socket against the action of a spring.

11. A surgical instrument as defined in claim 10 wherein said suction holder carries a sucker.

12. A surgical instrument as defined in claim 9 further comprising a device for generating a vacuum associated with said suction holder.

13. A surgical instrument as defined in claim 9 wherein said suction holder has a handle for displacement thereof.

14. A surgical instrument as defined in claim 9 wherein said suction holder is arranged in a central shaft of the surgical instrument.

15. A surgical instrument as defined in claim 1 wherein said striking surface is designed as a connection piece for a mechanically operated striking tool.

16. A surgical instrument as defined in claim 1 wherein said striking surface comprises a solid striking shaft for transmitting a striking force from a striking tool to said joint socket via said supports.

* * * * *